United States Patent [19]

Kuriyama et al.

[11] 4,363,812

[45] Dec. 14, 1982

[54] 3-(TETRAZOL-5-YL), 4-METHYL-8-ALKOXY COUMARINS AND ANTI-ALLERGIC COMPOSITIONS THEREOF

[75] Inventors: Kiyoshi Kuriyama, Takatsuki; Jun Nakano, Moriyama; Kiyonosin Itikawa, Otsu; Kiyoshi Ito, Otsu; Yuji Suzuki, Otsu; Katsuro Ishizuki, Otsu, all of Japan

[73] Assignee: Kakenyaku Kako Co., Ltd., Tokyo, Japan

[21] Appl. No.: 94,502

[22] Filed: Nov. 15, 1979

[30] Foreign Application Priority Data

Nov. 30, 1978 [JP] Japan .................. 53/149382

[51] Int. Cl.³ ..................... A61K 31/41; C07D 257/06
[52] U.S. Cl. ..................................... 424/269; 548/253
[58] Field of Search ................. 548/253; 424/269, 281

[56] References Cited

U.S. PATENT DOCUMENTS

| | | | |
|---|---|---|---|
| 2,683,720 | 7/1954 | Schlesinger et al. | 260/343.44 |
| 2,977,372 | 3/1962 | Finnegan et al. | 548/253 |
| 3,636,004 | 1/1972 | Bode et al. | 548/253 |
| 3,706,768 | 12/1972 | Bays | 548/252 |
| 4,059,704 | 11/1977 | Buckle et al. | 548/253 |
| 4,116,971 | 9/1978 | von Strandtmann et al. | 424/269 |

*Primary Examiner*—D. B. Springer
*Attorney, Agent, or Firm*—Armstrong, Nikaido, Marmelstein & Kubovcik

[57] ABSTRACT

Coumarin derivatives of the general formula:

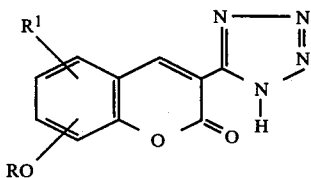

wherein R is hydrogen atom, an alkyl group or an alkenyl group, $R^1$ is hydrogen atom, an alkyl group, an alkenyl group or an alkoxy group, and the OR and $R^1$ groups each are substituted at any of the 5, 6, 7 and 8 positions of the coumarin ring, and the salt thereof. The compounds are useful as antiallergic agent for preventing and treating allergic diseases.

6 Claims, No Drawings

3-(TETRAZOL-5-YL), 4-METHYL-8-ALKOXY COUMARINS AND ANTI-ALLERGIC COMPOSITIONS THEREOF

BACKGROUND OF THE INVENTION

The present invention relates to novel coumarin derivatives and their salts, and further to a process for the preparation thereof and a pharmaceutical composition containing the coumarin derivatives.

It is known that a certain kind of coumarin derivatives have an antiallergic activity. For instance, Japanese Patent Unexamined Publication No. 64273/1975 discloses that coumarin compounds of the general formula (I):

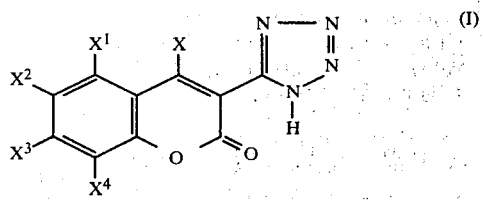

wherein X is an alkyl group or an aryl group, $X^1$, $X^2$, $X^3$ and $X^4$ are the same or different and each is hydrogen atom, nitro group, an alkyl group, an alkoxyl group, an aryl group, an aralkyl group, a heterocyclic group, a halogen atom, carboxyl group or an acyloxyl group, and any adjacent two groups of $X^1$, $X^2$, $X^3$ and $X^4$ may form a substituted or unsubstituted condensed carbon or heterocyclic ring with the carbon atoms bonding thereto, show an antiallergic action. However, these coumarin derivatives (I) are not always satisfactory antiallergic agents.

OBJECTS OF THE INVENTION

It is an object of the present invention to provide novel coumarin derivatives.

A further object of the invention is to provide coumarin derivatives useful as antiallergic agents.

A still further object of the invention is to provide a process for preparing coumarin derivatives.

Another object of the invention is to provide a pharmaceutical composition containing coumarin derivatives as active components which is useful for preventing and treating allergic diseases.

These and other objects of the invention will become apparent from the description hereinafter.

DETAILED DESCRIPTION

It has now been found that a coumarin derivative of the formula:

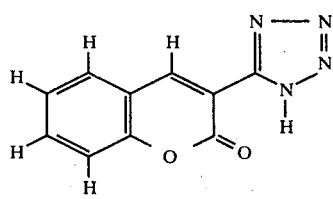

has a stronger antiallergic activity than the particular coumarin derivative shown by the before-mentioned general formula (I) wherein the substituent group X at the 4-position of the coumarin ring is methyl group and $X^1$, $X^2$, $X^3$ and $X^4$ all are hydrogen atom, and on the basis of this fact, it has also been found that coumarin derivatives having a further improved antiallergic activity and a decreased toxicity can be obtained by introducing specific groups, especially an alkoxy group, an alkenyloxy group, hydroxyl group or the like to any of the 5, 6, 7 and 8 positions of the coumarin ring of the above-mentioned coumarin derivative having no substituent group X at the 4-position.

According to the present invention, there are provided novel coumarin derivatives of the following general formula (II):

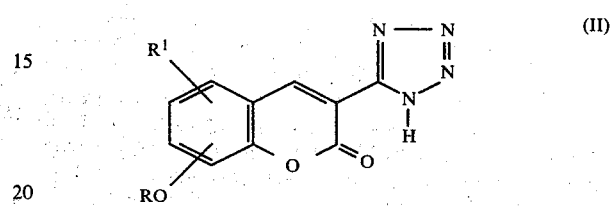

wherein R is hydrogen atom, an alkyl group or an alkenyl group, $R^1$ is hydrogen atom, an alkyl group, an alkenyl group or an alkoxyl group, and the OR and $R^1$ groups each are substituted at any of the 5, 6, 7 and 8 positions of the coumarin ring, and the salts thereof.

The alkyl group defined as R and $R^1$ in the above general formula (II) is a straight or branched alkyl group having 1 to 20 carbon atoms, such as methyl, ethyl, n-propyl, isopropyl, n-butyl, isobutyl, sec-butyl, tert-butyl, n-pentyl, isopentyl, sec-pentyl, neopentyl, tert-phenyl, n-hexyl, isohexyl, sec-hexyl, neohexyl, tert-hexyl, heptyl, 5-methylhexyl, octyl, nonyl, decyl, undecyl, dodecyl, tridecyl, tetradecyl, pentadecyl, hexadecyl, heptadecyl, octadecyl, nonadecyl or eicosyl group. The alkenyl group defined as R and $R^1$ is a straight or branched alkenyl group having 2 to 20 carbon atoms, such as vinyl, allyl, 1-propenyl, isopropenyl, 1-butenyl, 2-butenyl, 3-butenyl, isobutenyl, 1-pentenyl, 2-pentenyl, 3-pentenyl, 4-pentenyl, 3-methyl-2-butenyl, 2-methyl-3-butenyl, 1-hexenyl, 2-hexenyl, 3-hexenyl, 4-hexenyl, 5-hexenyl, 3-methyl-2-pentenyl, 2-methyl-2-pentenyl, 4-methyl-3-pentenyl, 3-methyl-3-pentenyl, 2-undecenyl, 2-dodecenyl, 2-tridecenyl, 2-tetradecenyl, 2-hexadecenyl, 9-octadecenyl, geranyl, 9,12-octadecadienyl, farnesyl or 9,12,15-octadecatrienyl group. The alkoxyl group defined as $R^1$ is a straight or branched alkoxyl group having 1 to 6 carbon atoms, such as methoxy, ethoxy, n-propoxy, isopropoxy, n-butoxy, isobutoxy, sec-butoxy, tert-butoxy, n-pentyloxy, isopentyloxy, sec-pentyloxy, neopentyloxy, tert-pentyloxy, n-hexyloxy, isohexyloxy, sec-hexyloxy, neohexyloxy or tert-hexyloxy group.

Suitable examples of the salts of the coumarin derivatives shown by the general formula (II) of the present invention are the pharmaceutically acceptable addition salts with ammonia or an amine such as ethanolamine, ethylamine, diethylamine, triethylamine or diisopropylamine, and the pharmaceutically acceptable metal salts such as the sodium, potassium, aluminum and calcium salts.

The preferred compounds among the coumarin derivatives (II) and their salts of the present invention are those beloging to the following classes:

(1) Coumarin derivatives defined by the general formula (II) wherein R is hydrogen atom, an alkyl group or an alkenyl group, and $R^1$ is hydrogen atom, and in particular, the OR group is substituted at the 7 or 8 position of the coumarin ring; and the slats thereof (2) Coumarin derivatives defined by the general formula (II) wherein R is hydrogen atom, an alkyl group or an alkenyl group, and $R^1$ is an alkyl group, and in particular, the OR and $R^1$ groups are substituted at the 6, 7 or 8 position of the coumarin ring; and the salts thereof (3) Coumarin derivatives defined by the general formula (II) wherein R is hydrogen, an alkyl group or an alkenyl group, and $R^1$ is an alkenyl group, and in particular, the OR group is substituted at the 7-position of the coumarin ring and the $R^1$ group is substituted at the 6-position of the coumarin ring; and the salts thereof (4) Coumarin derivatives defined by the general formula (II) wherein R is an alkyl group or an alkenyl group, and $R^1$ is an alkoxyl group, and in particular, the OR group is substituted at the 7-position of the coumarin ring and the $R^1$ group is substituted at the 5-position of the coumarin ring.

Suitable examples of the coumarin derivatives belonging to the above classes are 8-methoxy-3-(1H-tetrazol-5-yl)coumarin, 8-ethoxy-3-(1H-tetrazol-5-yl)coumarin, 8-n-propoxy-3-(1H-tetrazol-5-yl)coumarin, 8-isopropoxy-3-(1H-tetrazol-5-yl)coumarin, 7-n-propoxy-3-(1H-tetrazol-5-yl)coumarin, 8-n-butoxy-3-(1H-tetrazol-5-yl)coumarin, 8-n-pentyloxy-3-(1H-tetrazol-5-yl)coumarin, 8-isopentyloxy-3-(1H-tetrazol-5-yl)coumarin, 8-n-hexyloxy-3-(1H-tetrazol-5-yl)coumarin, 8-n-heptyloxy-3-(1H-tetrazol-5-yl)coumarin, 8-n-nonyloxy-3-(1H-tetrazol-5-yl)coumarin, 8-n-dodecyloxy-3-(1H-tetrazol-5-yl)coumarin, 8-n-pentadecyloxy-3-(1H-tetrazol-5-yl)coumarin, 8-n-octadecyloxy-3-(1H-tetrazol-5-yl)coumarin, 8-allyloxy-3-(1H-tetrazol-5-yl)coumarin, 8-geranyloxy-3-(1H-tetrazol-5-yl)coumarin, 8-farnesyloxy-3-(1H-tetrazol-5-yl)coumarin, 8-hydroxy-3-(1H-tetrazol-5-yl)coumarin, 8-ethoxy-6-methyl-3-(1H-tetrazol-5-yl)coumarin, 6-methyl-8-n-propoxy-3-(1H-tetrazol-5-yl)coumarin, 8-isopropoxy-6-methyl-3-(1H-tetrazol-5-yl)-coumarin, 8-n-butoxy-6-methyl-3-(1H-tetrazol-5-yl)coumarin, 6-ethyl-7-methoxy-3-(1H-tetrazol-5-yl)coumarin, 7-methoxy-8-methyl-3-(1H-tetrazol-5-yl)coumarin, 6-methoxy-7-methyl-3-(1H-tetrazol-5-yl)-coumarin, 8-allyloxy-6-methyl-3-(1H-tetrazol-5-yl)coumarin, 8-hydroxy-6-methyl-3-(1H-tetrazol-5-yl)coumarin, 7-methoxy-6-(3-methyl-2-butenyl)-3-(1H-tetrazol-5-yl)coumarin, 7-ethoxy-6-(3-methyl-2-butenyl)-3-(1H-tetrazol-5-yl)coumarin, 5,7-diethoxy-3-(1H-tetrazol-5-yl)coumarin, and their salts.

The coumarin derivatives (II) and their salts of the present invention have an excellent inhibitory effect on the isolation of chemical mediators such as histamine and slow reacting substance of anaphylaxis (SRS-A) from mast cells by immune reaction, and they are very useful as medicaments for prevention and treatment of allergic diseases such as allergic asthma, allergic rhinitis, urticaria, atopic dermatitis, ulcerative colitis and food allergy. In particular, the coumarin derivatives (II) having a substituent group of 6 or more carbon atoms and their salts have a marked effect on asthma. For instance, the oral administration of 8-n-hexyloxy-3-(1H-tetrazol-5-yl)coumarin shows a therapeutic effect in a test using a model of experimental asthma in animals. The effect on the prevention and treatment can be sufficiently exhibited by the dosage of about 0.05 to about 50 mg./day to adult.

The compounds of the present invention are characterized particularly by the fact that no substituent group is present at the 4-position of the coumarin ring, as compared with the compounds disclosed in Japanese Patent Unexamined Publication No. 64273/1975, and show a superior antiallergic activity. Moreover, the introduction of substituent groups such as an alkoxyl group, an alkenyloxy group and hydroxyl group to the 5, 6, 7 or 8 position of the coumarin ring brings the decrease of toxicity. With respect to the representative compounds of the present invention (Compounds A to H) and compounds disclosed to have particularly excellent effects in the above Japanese Publication (Compounds I and J), the results of the minimum effective dose (hereinafter referred to as "MED") orally in rats by a passive cutaneous anaphyaxis test and $LD_{50}$ (50% lethal dose) orally in mice are shown in Table 1 together with the safety margin ($LD_{50}$/MED) and the relative value of the safety margin to the Compound I of the Japanese Publication.

Compound A: 8-ethoxy-3-(1H-tetrazol-5-yl)coumarin

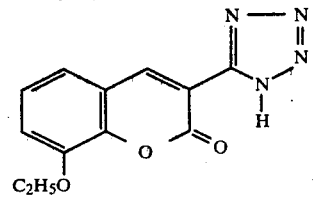

Compound B: 8-isopropoxy-3-(1H-tetrazol-5-yl)coumarin

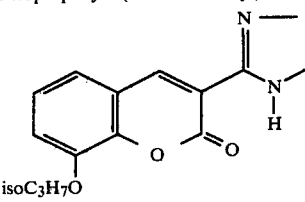

Compound C: 8-n-butoxy-3-(1H-tetrazol-5-yl)coumarin

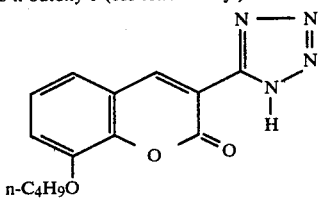

Compound D: 8-n-pentyloxy-3-(1H-tetrazol-5-yl)coumarin

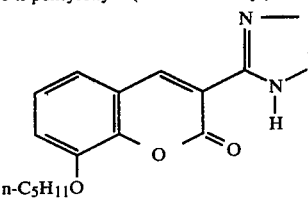

Compound E: 8-n-hexyloxy-3-(1H-tetrazol-5-yl)coumarin

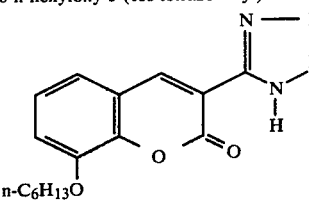

Compound F: 8-ethoxy-6-methyl-3-(1H-tetrazol-5-yl)coumarin

-continued

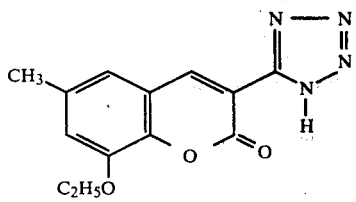

Compound G: 8-isopropoxy-6-methyl-3-(1H-tetrazol-5-yl)-coumarin

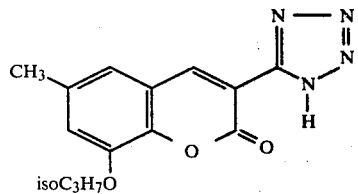

Compound H: 8-n-butoxy-6-methyl-3-(1H-tetrazol-5-yl)-coumarin

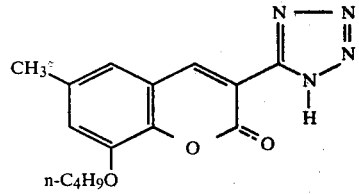

Compound I: 8-chloro-4-methyl-3-(1H-tetrazol-5-yl)coumarin

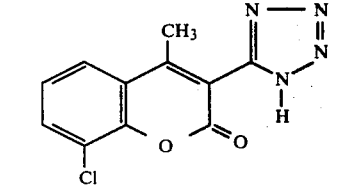

Compound J: 4,6-dimethyl-3-(1H-tetrazol-5-yl)coumarin

TABLE 1

|  | Compound | MED mg./kg. | LD$_{50}$ mg./kg. | Safety margin (LD$_{50}$/ MED) | Relative value of safety margin |
|---|---|---|---|---|---|
|  | A | 6.25 | 2500 | 400 | 2.4 |
|  | B | 1.56 | 2250 | 1442 | 8.6 |
|  | C | 1.56 | 2380 | 1526 | 9.1 |
| Compounds | D | 1.56 | 1330 | 853 | 5. |
| of the | E | 1.56 | 2650 | 1699 | 10.2 |
| invention | F | 1.56 | 2360 | 1513 | 9.1 |
|  | G | 1.56 | 2200 | 1410 | 8.4 |
|  | H | 0.39 | 1870 | 4795 | 28.7 |
| Compounds of Jap. | I | 6.25 | 1045 | 167 | 1.0 |
| Pub. No. 64273/75 | J | 25.00 | 533 | 21 | 0.3 |

As is clear from Table 1, the compounds (II) of the present invention have a broader safety margin than the compounds (I) of Japanese Patent Unexamined Publication No. 64273/1975, and are excellent antiallergic agents which can be used with safety as medicaments.

The coumarin derivatives (II) and their salts of the present invention are prepared by reacting 3-cyanocoumarin derivatives of the following formula (III):

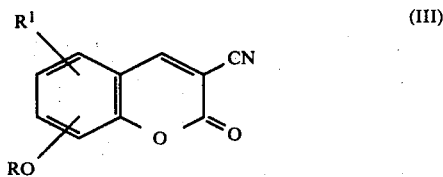

wherein R and R$^1$ are as defined above, with hydrazoic acid or its salts.

Examples of the salt of hydrazoic acid employed in the reaction are the alkali metal salts such as lithium azide, sodium azide and potassium azide, the alkaline earth metal salts such as magnesium azide, calcium azide, barium azide and strontium azide, other metal salts such as aluminum azide, tin azide, zinc azide and titanium azide, and the salts with organic bases such as ammonium azide and anilinium azide. These hydrazoic acid salts may be employed alone, and also, some of the hydrazoic acid salts, e.g. the alkali metal salts such as sodium azide, may be employed in combination with ammonium chloride or a Lewis acid such as aluminum chloride, stannic chloride, zinc chloride or titanium tetrachloride, In that case, the hydrazoic acid salt with an alkali metal reacts with ammonium chloride or the Lewis acid to produce another corresponding hydrazoic acid salt such as ammonium azide, aluminum azide, tin azide, zinc azide or titanium azide, and the produced hydrazoic acid salt reacts with the 3-cyano-coumarin derivative (III). The combination use of the hydrazoic acid alkali metal salt with ammonium chloride or the Lewis acid produces a particularly good result.

The amounts of hydrazoic acid or its salts and the Lewis acids or ammonium chloride used in combination with the salts are usually selected from 1 to 10 moles per mole of the 3-cyano-coumarin derivative (III), respectively.

The reaction is usually carried out in an organic solvent such as hydrocarbons, e.g. benzene, toluene and petroleum ether, ethers, e.g. tetrahyrofuran, dioxane and ethyl ether, or aprotic polar solvents, e.g. dimethylformamide and dimethyl sulfoxide.

The reaction conditions such as temperature and time are not particularly limited, but the reaction is usually carried out at a temperature of room temperature to 130° C. for 30 minutes to 24 hours.

When the hydrazoic acid salt is employed in the reaction, the intended compound is produced in the form of a salt corresponding to the hydrazoic acid salt used in the reaction, on the basis of the acidic property of the tetrazolyl group. The salt may be isolated as it is, or may be treated with a mineral acid such as hydrochloric acid or sulfuric acid to give the compound of the general formula (II) having a free tetrazolyl group.

The products may be isolated and purified in a usual manner, such as fractionation based on dissociation of hydrogen of tetrazolyl group, chromatography or recrystallization.

Although the salts of the coumarin derivatives (II) of the invention are directly obtained by the above reaction, they may be obtained by once isolating the coumarin derivatives (II) and reacting them with a corresponding base.

With respect to the 3-cyanocoumarin derivatives (III) employed as the starting materials for preparing the coumarin derivatives (II) and their salts of the invention, a part of them are known, but a part of them are novel compounds. The novel 3-cyanocoumarin derivatives (III) can be readily prepared by reacting o-hydroxybenzaldehyde derivatives of the following general formula (IV):

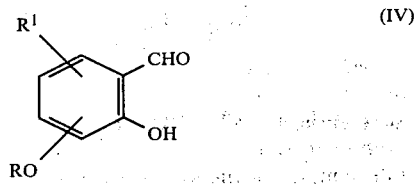

wherein R and R$^1$ are as defined above, with cyanomalonic esters, e.g. cyanomalonic esters with lower alcohols such as methyl alcohol and ethyl alcohol, or malononitrile.

Also, among the 3-cyanocoumarin derivatives (III), 3-cyanocoumarin derivatives of the following general formula (V):

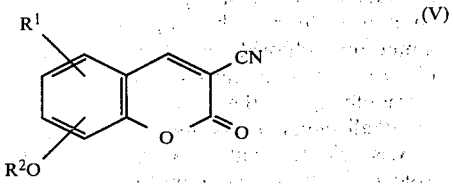

wherein R$^1$ is as defined above, R$^2$ is an alkyl group or an alkenyl group, and the OR$^2$ group is substituted at the 5, 6, 7 or 8 position of the coumarin ring, are also prepared by reacting 3-cyanocoumarin derivatives of the following general formula (VI):

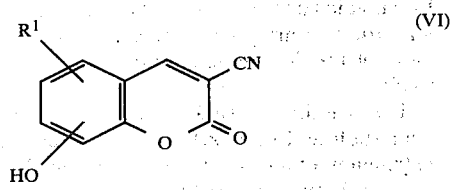

wherein R$^1$ is as defined above, and OH group is substituted at the 5, 6, 7 or 8 position of the coumarin ring, with halogen compounds of the following general formula (VII):

R$^2$Y   (VII)

wherein R$^2$ is as defined above and Y is a halogen atom, in the presence of alkali metal hydrides such as sodium hydride and potassium hydride. The above 3-cyanocoumarin derivatives (VI) can be prepared in the above-mentioned manner by the reaction of the o-hydroxy-benzaldehyde derivatives (IV) and the cyanomalonic esters or malononitrile.

The coumarin derivatives (II) and their pharmaceutically acceptable salts of the present invention exhibit excellent activities, particularly in oral administration, and can be formulated in a usual manner into compositions in the form of tablet, capsule, powder and granule with conventional pharmaceutical carriers. They are also usable as an aerosol in the form of solution or suspension. The salts of the coumarin derivatives (II) are soluble in water and, therefore, can also be employed in liquid form such as for injections, sirup or nasal drops. Any conventional carriers employed in preparing preparations can be employed in the present invention. Examples of the carrier are binders, solid diluents, liquid diluents, fillers and the like, such as starch, lactose, microcrystalline cellulose, sugar, magnesium stearate, silicon dioxide, talc and physiological salt solution.

The present invention is more particularly described and explained by means of the following Examples, in which all % and parts are by weight unless otherwise noted. In order to illustrate the preparation of the 3-cyanocoumarin derivatives (III) employed as the starting materials for preparing the coumarin derivatives (II) and their salts of the invention, the following Reference Examples are also presented.

REFERENCE EXAMPLE 1

[3-Cyano-8-ethoxycoumarin]

In 100 ml. of ethanol was dissolved 16.6 g. of 3-ethoxy-2-hydroxybenzaldehyde. After adding 11.5 g. of ethyl cyanomalonate to the solution, two drops of piperidine were added. The mixture was refluxed for 2 hours with agitation. After the completion of the reaction, the reaction mixture was cooled with water and the precipitated yellow product was separated by filtration. The obtained yellow powder was agitated with hot acetone, and the insoluble material was removed by filtration. The filtrate was concentrated and cooled with water, and the precipitated product was filtered to give 6.4 g. of 3-cyano-8-ethoxycoumarin in the form of light yellow powder. The melting point was 182° to 184° C. (decomposition).

Analysis for $C_{12}H_9NO_3$: Calcd. (%): C; 66.97, H; 4.22, N; 6.51 Found (%): C; 66.81, H; 4.30, N; 6.46

Infrared absorption spectrum ($\nu_{max}^{KBr}$ cm.$^{-1}$): 2,220 (CN), 1,715 (C=O), 1,600 and 1,570 (C=C)

Mass spectrum (M/e): 215 (M+), 187 and 159

REFERENCE EXAMPLE 2

[3-Cyano-7-methoxy-8-methylcoumarin]

In 20 ml. of ethanol was dissolved 1.66 g. of 2-hydroxy-4-methoxy-3-methylbenzaldehyde, and thereto was added 0.66 g. of malononitrile which was dissolved at 50° C. To the solution, two drops of piperidine were added and agitated for 1 minute, and further 2 ml. of concentrated hydrochloric acid was added and agitated for 3 minutes. After the completion of the reaction, the reaction mixture was cooled with ice. The resulting precipitate was filtered and washed with water, and was then recrystallized from ethanol to give 1.4 g. of 3-cyano-7-methoxy-8-methylcoumarin in the form of light yellow needles. The melting point was 215° C.

Analysis for $C_{12}H_9NO_3$: Calcd. (%): C; 66.97, H; 4.22, N; 6.51 Found (%): C; 66.71, H; 4.28, N; 6.45

Infrared absorption spectrum ($\nu_{max}^{KBr}$ cm.$^{-1}$): 2,240 (CN), 1,730 (C=O), 1,615, 1,605 and 1,565 (C=C)

Mass spectrum (M/e): 215 (M+), 200, 187 and 172

REFERENCE EXAMPLES 3 TO 10

The procedures of Reference Example 1 or 2 were repeated except that there was employed as the starting material 2-hydroxy-3-methoxybenzaldehyde (Ref. Ex. 3), 5-ethyl-2-hydroxy-4-methoxybenzaldehyde (Ref.

Ex. 4), 2-hydroxy-5-methoxy-4-methylbenzaldehyde (Ref. Ex. 5), 2-hydroxy-4-methoxy-5-(3-methyl-2-butenyl)benzaldehyde (Ref. Ex. 6), 4-ethoxy-2-hydroxy-5-(3-methyl-2-butenyl)benzaldehyde (Ref. Ex. 7), 4,6-diethoxy-2-hydroxybenzaldehyde (Ref. Ex. 8), 2,3dihydroxybenzaldehyde (Ref. Ex. 9), or 2,3-dihydroxy-5-methylbenzaldehyde (Ref. Ex. 10), to give the following products.

The results are shown below, in which the solvent enclosed in parentheses after crystal form shows solvent used in recrystallization.

(Ref. Ex. 3) 3-Cyano-8-methoxycoumarin

Light yellow needles (ethanol)
Melting point: 223° to 226° C. (decomposition)
Analysis for $C_{11}H_7NO_3$ Calcd. (%): C; 65.67, H; 3.51, N; 6.96. Found (%): C; 65.41, H; 3.63, N; 6.61.
Infrared absorption spectrum $(\nu_{max}^{KBr}$ cm.$^{-1})$: 2.240 (CN), 1,735 (C=O), 1,605 and 1,570 (C=C)
Mass spectrum (M/e): 201 (M+), 186, 173, 158 and 130

(Ref. Ex. 4) 3-Cyano-6-ethyl-7-methoxycoumarin

Yellow needles (ethanol)
Melting point: 210° C.
Analysis for $C_{13}H_{11}NO_3$: Calcd. (%): C; 68.11, H; 4.84, N; 6.11. Found (%): C; 68.02, H; 4.85, N; 6.04.
Infrared absorption spectrum $(\nu_{max}^{KBr}$ cm.$^{-1})$: 2,240 (CN), 1,730, 1,720 (C=O), 1,620, 1,605 and 1,565 (C=C)
Mass spectrum (M/e): 229 (M+), 214, 186, 184 and 156

(Ref. Ex. 5) 3-Cyano-6-methoxy-7-methylcoumarin

Yellow needles (ethanol)
Melting point: 197° to 198° C.
Analysis for $C_{12}H_9NO_3$: Calcd. (%): C; 66.97, H; 4.22, N; 6.51. Found (%): C; 66.71, H; 4.27, N; 6.34.
Infrared absorption spectrum $(\nu_{max}^{KBr}$ cm.$^{-1})$: 2,240 (CN), 1,730 (C=O), 1,610 and 1,600 (C=C)
Mass spectrum (M/e): 215 (M+), 200, 187 and 172

(Ref. Ex. 6) 3-Cyano-7-methoxy-6-(3-methyl-2-butenyl)-coumarin

Light yellow needles (ethyl acetate)
Melting point: 181° to 182° C.
Analysis for $C_{16}H_{15}NO_3$: Calcd. (%): C; 71.36, H; 5.61, N; 5.20. Found (%): C; 71.17, H; 5.70, N; 5.04.
Infrared absorption spectrum $(\nu_{max}^{KBr}$ cm.$^{-1})$: 2,220 (CN), 1,735, 1,715 (C=O), 1,620 and 1,600 (C=C)
Mass spectrum (M/e): 269 (M+), 254 and 214

(Ref. Ex. 7) 3-Cyano-7-ethoxy-6-(3-methyl-2-butenyl)-coumarin

Light yellow needles (ethyl acetate)
Melting point: 187° to 188° C.
Analysis for $C_{17}H_{17}NO_3$: Calcd. (%): C; 72.06, H; 6.05, N; 4.97. Found (%): C; 72.01, H; 6.06, N; 4.87.
Infrared absorption spectrum $(\nu_{max}^{KBr}$ cm$^{-1})$: 2,220 (CN), 1,735, 1,715 (C=O), 1,620 and 1,600 (C=C)
Mass spectrum (M/e): 283 (M+), 268, 254, 239, 228 and 226

(Ref. Ex. 8) 3-Cyano-5,7-diethoxycoumarin

Yellow needles (ethanol)
Melting point: 215° C.
Analysis for $C_{14}H_{13}NO_3$: Calcd. (%): C; 64.86, H; 5.05, N; 5.40. Found (%): C 64.66, H; 5.13, N; 5.29.
Infrared absorption spectrum $(\nu_{max}^{KBr}$ cm.$^{-1})$: 2,220 (CN), 1,730 (C=O), 1,620, 1,605 and 1,560 (C=C)
Mass spectrum (M/e): 259 (M+), 231, 203 and 175

(Ref. Ex. 9) 3-Cyano-8-hydroxycoumarin

Yellow needles (acetone)
Melting point: 151° to 153° C.
Analysis for $C_{10}H_5NO_3$: Calcd. (%): C; 164.17, H; 2.69, N; 7.48. Found (%): C; 64.03, H; 2.75, N; 7.17.
Infrared absorption spectrum $(\nu_{max}^{KBr}$ cm.$^{-1})$: 3,050 (OH), 2,230 (CN), 1,715 (C=O), 1,610 and 1,570 (C=C)
Mass spectrum (M/e): 187 (M+), 159 and 131 (Ref. Ex. 10) 3-Cyano-8-hydroxy-6-methylcoumarin Yellow needles (acetone)
Melting point: 260° to 261° C.
Analysis for $C_{11}H_7NO_3$: Calcd. (%): C; 65.57, H; 3.51, N; 6.96. Found (%): C; 65.48, H; 3.63, N; 6.76.
Infrared absorption spectrum $(\nu_{max}^{KBr}$ cm.$^{-1})$: 3,250 (OH), 2,250 (CN), 1,705 (C=O), 1,625 and 1,585 (C=C)
Mass spectrum (M/e): 201 (M+), 173, 172 and 145

REFERENCE EXAMPLE 11

[3-Cyano-8-ethoxy-6-methylcoumarin]

In 20 ml. of dry dimethylformamide was dissolved 4 g. of 3-cyano-8-hydroxy-6-methylcoumarin, and 0.96 g. of sodium hydride (60% in oil suspension) was then added to the solution with agitation and ice cooling. The agitation was further continued for 20 minutes. The temperature was then elevated and 3.7 g. of ethyl iodide was added dropwise at 50° C. with agitation. After the completion of the addition, the agitation was further continued for 5 hours at 50° C. The thus obtained reaction mixture was poured into 100 ml. of 10% hydrochloric acid added with ice, and the resulting precipitate was filtered. The precipitate was recrystallized from ethanol to give 4.5 g. of 3-cyano-8-ethoxy-6-methylcoumarin in the form of light yellow needles. The melting point was 173° C.
Analysis for $C_{13}H_{11}NO_3$: Calcd. (%): C; 68.11, H; 4.84, N; 6.11. Found (%): 67.88, H; 4.91, N; 5.96.
Infrared absorption spectrum $(\nu_{max}^{KBr}$ cm.$^{-1})$: 2,240 (CN), 1,735 (C=O), 1,615, 1,595 and 1,680 (C=C)
Mass spectrum (M/e): 229 (M+), 201, 173 and 172

REFERENCE EXAMPLE 12 TO 30

The procedures of Reference Example 11 were repeated except that the compounds shown in Table 2 were employed as the starting materials.

With respect to Reference Examples 19 to 23, 25 and 26, the precipitate was purified by means of a silica gel column chromatography (eluent: methylene chloride/n-hexane=1/1 by volume).

TABLE 2

| Ref. Ex. No. | Coumarin derivatives (VI) | Halide (VII) |
|---|---|---|
| 12 | 3-cyano-8-hydroxycoumarin | n-propyl iodide |
| 13 | " | isopropyl iodide |
| 14 | 3-cyano-7-hydroxycoumarin | n-propyl iodide |
| 15 | 3-cyano-8-hydroxycoumarin | n-butyl iodide |
| 16 | " | n-pentyl iodide |
| 17 | " | isopenty iodide |
| 18 | " | n-hexyl iodide |
| 19 | " | n-heptyl bromide |
| 20 | 3-cyano-8-hydroxycoumarin | n-nonyl bromide |
| 21 | " | n-dodecyl bromide |
| 22 | " | n-pentadecyl bromide |
| 23 | " | n-octadecyl bromide |

TABLE 2-continued

| Ref. Ex. No. | Coumarin derivatives (VI) | Halide (VII) |
|---|---|---|
| 24 | " | allyl bromide |
| 25 | " | geranyl bromide |
| 26 | " | farnesyl bromide |
| 27 | 3-cyano-8-hydroxy-6-methyl-coumarin | n-propyl iodide |
| 28 | " | isopropyl iodide |
| 29 | " | n-butyl iodide |
| 30 | " | allyl bromide |

The products and the results of analysis are as follows:

(Ref. Ex. 12) 3-Cyano-8-n-propoxycoumarin

Light yellow needles (ethanol)
Melting point: 157° to 158° C.
Analysis for $C_{13}H_{11}NO_3$: Calcd. (%): C; 68.11, H; 4.84, N; 6.11. Found (%): C; 67.88, H; 4.95, N; 6.02.
Infrared absorption spectrum $(\nu_{max}^{KBr} \text{ cm.}^{-1})$: 2,240 (CN), 1,735 (C=O), 1,610 and 1,570 (C=C)
Mass spectrum (M/e): 229 (M+), 212, 201, 187 and 159

(Ref. Ex. 13) 3-Cyano-8-isopropoxycoumarin

Light yellow needles (ethanol)
Melting point: 129° C.
Analysis for $C_{13}H_{11}NO_3$: Calcd. (%): C; 68.11, H; 4.84, N; 6.11. Found (%): C; 68.03, H; 4.90, N; 6.05.
Infrared absorption spectrum $(\nu_{max}^{KBr} \text{ cm.}^{-1})$: 2,240 (CN), 1,735 (C=O), 1,605 and 1,570 (C=C)
Mass spectrum (M/e): 229 (M+); 214, 188, 187 and 159

(Ref. Ex. 14) 3-Cyano-7-m-propoxycoumarin

Light yellow needles (ethanol)
Melting point: 162° to 163° C.
Analysis for $C_{13}H_{11}NO_3$: Calcd. (%): C 68.11, H 4.84, N 6.11. Found (%): C 67.78. H 4.98, N 5.92.
Infrared absorption spectrum $(\nu_{max}^{KBr} \text{ cm.}^{-1})$: 2,220 (CN), 1,720 (C=O), 1,615 and 1,595 (C=C)
Mass spectrum (M/e): 229 (M+), 214, 201, 187 and 159

(Ref. Ex. 15) 8-n-Butoxy-3-cyanocoumarin

Light yellow needles (ethyl acetate)
Melting point: 94° to 95° C.
Analysis for $C_{14}H_{13}NO_3$: Calcd. (%): C 69.12, H 5.39, N 5.76. Found (%): C 69.07, H 5.43, N 5.61.
Infrared absorption spectrum $(\nu_{max}^{KBr} \text{ cm.}^{-1})$: 2,230 (CN), 1,730 (C=O), 1,605 and 1,570 (C=C)
Mass spectrum (M/e): 243 (M+), 201, 188, 187 and 159

(Ref. Ex. 16) 3-Cyano-8-n-pentyloxycoumarin

Light yellow needles (ethyl acetate)
Melting point: 87° C.
Analysis for $C_{15}H_{15}NO_3$: Calcd. (%): C 70.02, H 5.88, N 5.44. Found (%): C 69.83, H 5.97, N 5.19.
Infrared absorption spectrum $(\nu_{max}^{KBr} \text{ cm.}^{-1})$: 2,220 (CN), 1,730 (C=O), 1,605 and 1,570 (C=C)
Mass spectrum (M/e): 257 (M+), 188, 187 and 159

(Ref. Ex. 17) 3-Cyano-8-isopentyloxycoumarin

Light yellow needles (benzene)
Melting point: 104° C.
Analysis for $C_{15}H_{15}NO_3$: Calcd. (%): C 70.02, H 5.88, N 5.44. Found (%): C 69.94, H 5.90, N 5.33.
Infrared absorption spectrum $(\nu_{max}^{KBr} \text{ cm.}^{-1})$: 2,230 (CN), 1,730 (C=O), 1,605 and 1,570 (C=C)
Mass spectrum (M/e): 257 (M+), 188, 187, 159 and 131

(Ref. Ex. 18) 3-Cyano-8-n-hexyloxycoumarin

Light yellow needles (benzene)
Melting point: 81° to 82° C.
Analysis for $C_{16}H_{17}NO_3$: Calcd. (%): C 70.83, H 6.32, N 5.16. Found (%): C 70.54, H 6.41, N 4.93.
Infrared absorption spectrum $(\nu_{max}^{KBr} \text{ cm.}^{-1})$: 2,230 (CN), 1,740 and 1,730 (C=O), 1,605 and 1,570 (C=C)
Mass spectrum (M/e): 271 (M+), 188, 187 and 159

(Ref. Ex. 19) 3-Cyano-8-n-heptyloxycoumarin

Light yellow needles (benzene)
Melting point: 97° C.
Analysis for $C_{17}H_{19}NO_3$: Calcd. (%): C 71.56, H 6.71, N 4.91. Found (%): C 71.41, H 6.73, N, 4.87.
Infrared absorption spectrum $(\nu_{max}^{KBr} \text{ cm.}^{-1})$: 2,230 (CN), 1,735 (C=O), 1,605 and 1,570 (C=C)
Mass spectrum (M/e): 285 (M+), 188, 187 and 159

(Ref. Ex. 20) 3-Cyano-8-n-nonyloxycoumarin

Light yellow needles (benzene)
Melting point: 99° to 100° C.
Analysis for $C_{19}H_{23}NO_3$: Calcd. (%): C 72.82, H 7.40, N 4.47. Found (%): C 72.69, H 7.47, N 4.41.
Infrared absorption spectrum $(\nu_{max}^{KBr} \text{ cm.}^{-1})$: 2,220 (CN), 1,735 (C=O), 1,600 and 1,565 (C=C)
Mass spectrum (M/e): 313 (M+), 188 and 187

(Ref. Ex. 21) 3-Cyano-8-n-dodecyloxycoumarin

Light yellow needles (benzene/n-hexane=4/1 by volume)
Melting point: 106° C.
(Analysis for $C_{22}H_{29}NO_3$: Calcd. (%): C 74.33, H 8.22, N 3.94. Found (%): C 74.25, H 8.26, N 3.87.
Infrared absorption spectrum $(\nu_{max}^{KBr} \text{ cm.}^{-1})$: 2,240 (CN), 1,730 (C=O), 1,610 and 1,570 (C=C)
Mass spectrum (M/e): 355 (M+), 188 and 187

(Ref. Ex. 22) 3-Cyano-8-n-pentadecyloxycoumarin

Light yellow needles (benzene/n-hexane=3/1 by volume)
Melting point: 106° C.
Analysis for $C_{25}H_{35}NO_3$: Calcd. (%): C 75.53, H 8.87, N 3.52. Found (%): C 75.42, H 8.95, N 3.49.
Infrared absorption spectrum $(\nu_{max}^{KBr} \text{ cm.}^{-1})$: 2,230 (CN), 1,735 (C=O), 1,605 and 1,570 (C=C)
Mass spectrum (M/e): 397 (M+), 188 and 187

(Ref. Ex. 23) 3-Cyano-8-n-octadecyloxycoumarin

Light yellow needles (benzene/n-hexane=3/1 by volume)
Melting point: 112° C.
Analysis for $C_{28}H_{41}NO_3$: Calcd. (%): C 76.49, H 9.40, N 3.19. Found (%): C 76.40, H 9.45, N 3.11.
Infrared absorption spectrum $(\nu_{max}^{KBr} \text{ cm.}^{-1})$: 2,240 (CN), 1,730 (C=O), 1,605 and 1,570 (C=C)
Mass spectrum (M/e): 439 (M+), 188 and 187

(Ref. Ex. 24) 8-Allyloxy-3-cyanocoumarin

Colorless needles (ethyl acetate)
Melting point: 162° to 163° C.

Analysis for $C_{13}H_9NO_3$: Calcd. (%): C 68.72, H 3.99, N 6.17. Found (%): C 68.48, H 4.01, N 6.11.
Infrared absorption spectrum ($\nu_{max}^{KBr}$ cm.$^{-1}$): 2,240 (CN), 1,735 (C=O), 1,610 and 1,570 (C=C)
Mass spectrum (M/e): 227 (M+), 187, 159 and 158

(Ref. Ex. 25) 3-Cyano-8-geranyloxycoumarin

Light yellow needles (benzene/n-hexane=1/1 by volume)
Melting point: 82° C.
Analysis for $C_{20}H_{21}NO_3$: Calcd. (%): C 74.28, H 6.55, N 4.33. Found (%): C 74.14, H 6.59, N 4.24.
Infrared absorption spectrum ($\nu_{max}^{KBr}$ cm.$^{-1}$): 2,220 (CN), 1,720 (C=O), 1,600 and 1,570 (C=C)
Mass spectrum (M/e): 323 (M+), 254, 187 and 147

(Ref. Ex. 26) 3-Cyano-8-farnesyloxycoumarin

Lighe yellow oil
Analysis for $C_{25}H_{29}NO_3$: Calcd. (%): C 76.69, H 7.47, N 3.58. Found (%): C 76.52, H 7.51, N 3.52.
Infrared absorption spectrum ($\nu_{max}^{KBr}$ cm.$^{-1}$): 2,230 (CN), 1,730 (C=O), 1,605 and 1,570 (C=C)
Mass spectrum (M/e): 391 (M+), 348, 205 and 146

(Ref. Ex. 27) 3-Cyano-6-methyl-8n-propoxycoumarin

Yellow needles (ehanol)
Melting point: 173° to 174° C.
Analysis for $C_{14}H_{13}NO_3$: Calcd. (%): C 69.12, H 5.39, N 5.76. Found (%): C 69.04, H 5.42, N 5.50.
Infrared absorption spectrum ($\nu_{max}^{KBr}$ cm.$^{-1}$): 2,230 CN), 1,740 (C=O), 1,620, 1,595 and 1,580 (C=C)
Mass spectrum (M/e): 243 (M+), 201 and 173

Ref. Ex. 28) 3-Cyano-8-isopropoxy-6-methylcoumarin

Light yellow needles (acetone)
Melting point: 150° C.
Analysis for $C_{14}H_{13}NO_3$: Calcd. (%): C 69.12, H 5.39, N 5.76. Found (%): C 69.06, H 5.40, N 5.63.
Infrared absorption spectrum ($\nu_{max}^{KBr}$ cm.$^{-1}$): 2,240 (CN), 1,735 (C=O), 1,615, 1,595 and 1,580 (C=C)
Mass spectrum (M/e): 286 (M+), 272, 244, 202, 201, 160 and 132

(Ref. Ex. 29) 8-n-Butoxy-3-cyano-6-methylcoumarin

Light yellow needles (benzene)
Melting point: 170° C.
Analysis for $C_{15}H_{15}NO_3$: Calcd. (%): C 70.02, H 5.88, N 5.44. Found (%): C 69.83, H 5.95, N 5.32.
Infrared absorption spectrum ($\nu_{max}^{KBr}$ cm.$^{-1}$): 2,240 (CN), 1,740 (C=O), 1,615 and 1,585 (C=C)
Mass spectrum (M/e): 257 (M+), 201, 173 and 145

(Ref. Ex. 30) 8-Allyloxy-3-cyano-6-methylcoumarin

Light yellow needles (ethyl acetate)
Melting point: 125° to 127° C.
Analysis for $C_{14}H_{11}NO_3$: Calcd. (%): C 69.70, H 4.59, N, 5.80. Found (%): C 69.49, H, 4.66, N 5.54.
Infrared absorption spectrum ($\nu_{max}^{KBr}$ cm.$^{-1}$): 2,240 (CN), 1,740 (C=O), 1,620, 1,595 and 1,580 (C=C)
Mass spectrum (M/e): 248 (M+), 241, 201 and 200

EXAMPLE 1

[8-n-Pentyloxy-3-(1H-tetrazol-5-yl)coumarin]

To 50 ml. of anhydrous tetrahydrofuran was added 8 g. of aluminum chloride with ice cooling, and further 11.7 g. of sodium azide and 5.1 g. of 3-cyano-8-n-pentyloxycoumarin were added in that order. The mixture was refluxed for 5 hours with agitation. After the completion of the reaction, the reaction mixture was poured into 200 ml. of 10% hydrochloric acid added with ice and was thoroughly agitated. The resulting precipitate was filtered and was then added to 100 ml. of a saturated aqueous solution of sodium hydrogencarbonate. After dissolving the precipitate with heating and agitation, insoluble material was removed by filtration. A concentrated hydrochloric acid was gradually added dropwise to the filtrate to adjust to pH 3 to 4, and the resulting precipitate was filtered. The obtained light yellow precipitate was dissolved in a dimethylformamide-water mixed solvent (4:1 by volume) (hereinafter referred to as "DMF-H$_2$O"), and after treating with active carbon, was recrystallized to give 4 g. of 8-n-pentyloxy-3-(1H-tetrazol-5-yl)coumarin in the form of light yellow needles. The melting point was 199° C. (decomposition).
Analysis for $C_{15}H_{16}N_4O_3$: Calcd. (%): C 59.99, H 5.37, N 18.66. Found (%): C 59.78, H 5.46, N 18.45.
Infrared absorption spectrum ($\nu_{max}^{KBr}$ cm.$^{-1}$): 3,150 (NH), 1,720 (C=O), 1,615, 1,595 and 1,580 (C=C)
Mass spectrum (M/e): 300 (M+), 272, 244, 231, 230, 146 and 118

EXAMPLE 2

[8-n-Butoxy-6-methyl-3-(1H-tetrazol-5-yl)coumarin]

To 50 ml. of anhydrous tetrahydrofuran was added 8 g. of aluminum chloride with ice cooling, and further 11.7 g. of sodium azide and 5.1 g. of 8-n-butoxy-3-cyano-6-methylcoumarin were added in that order. The mixture was refluxed for 4 hours with agitation. After the completion of the reaction, the reaction mixture was poured into 200 ml. of 10% hydrochloric acid added with ice and was thoroughly agitated. The resulting precipitate was filtered and was then added to 100 ml. of a saturated aqueous solution of sodium hydrogencarbonate, to which 100 ml. of water was further added. The precipitate was dissolved with heating and agitation, and insoluble material was removed by filtration. The filtrate was adjusted to pH 3 to 4 by gradually adding dropwise a concentrated hydrochloric acid, and the resulting precipitate was filtered. The obtained light yellow precipitate was dissolved in a DMF-H$_2$O mixed solvent (5:1 by volume), and after treating with active carbon, was recrystallized to give 4.2 g. of 8-n-butoxy-6-methyl-3-(1H-tetrazol-5-yl)coumarin in the form of light yellow needles. The melting point was 242° to 243° C. (decomposition).
Analysis for $C_{15}H_{16}N_4O_3$: Calcd. (%): C 59.99, H 5.37, N 18.66. Found (%): C 59.85, H 5.41, N 18.54.
Infrared absorption spectrum ($\nu_{max}^{KBr}$ cm.$^{-1}$): 3,200 (NH), 1,700 (C=O), 1,620, 1,605 and 1,585 (C=C)
Mass spectrum (M/e): 300 (M+), 272, 258, 257, 244, 202, 201, 160 and 132

EXAMPLES 3 TO 30

The procedures of Example 1 or 2 were repeated except that there was employed as the starting material 3-cyano-8-methoxycourmarin (Ex. 3), 3-cyano-8-ethoxycoumarin (Ex. 4), 3-cyano-8-n-propoxycoumarin (Ex. 5), 3-cyano-8-isopropoxycoumarin (Ex. 6), 3-cyano-7-n-propoxycoumarin (Ex. 7), 8-n-butoxy-3-cyanocomarin (Ex. 8), 3-cyano-8-isopentyloxycoumarin (Ex. 9), 3-cyano-8-n-hexyloxycoumarin (Ex. 10), 3-cyano-8-n-heptyloxycoumarin (Ex. 11), 3-cyano-8-n-nonyloxycoumarin (Ex. 12), 3-cyano-8-n-dodecyloxycoumarin (Ex. 13), 3-cyano-n-pentadecyloxycoumarin (Ex. 14), 3-cyano-8-n-octadecyloxycoumarin (Ex. 15), 8-allyloxy-3-cyanocoumarin (Ex. 16), 3-cyano-8-geranyloxycoumarin (Ex. 17), 3-cyano-8-farnesyloxycoumarin (Ex. 18), 3-cyano-8-hydroxycoumarin (Ex. 19), 3-cyano-8-ethoxy-6-methylcoumarin (Ex. 20), 3-cyano-6-methyl-8-n-propoxycoumarin (Ex. 21), 3-cyano-8-isopropoxy-6-methylcoumarin (Ex. 22), 3-cyano-6-ethyl-7-methoxycoumarin (Ex. 23), 3-cyano-7-methoxy-8-methylcoumarin (Ex. 24), 3-cyano-6-methoxy-7-methylcoumarin (Ex. 25), 8-allyloxy-3-cyano-6-methylcoumarin (Ex. 26), 3-cyano-8-hydroxy-6-methylcoumarin (Ex. 27), 3-cyano-7-methoxy-6-(3-methyl-2-butenyl)coumarin (Ex. 28), 3-cyano-7-ethoxy-6-(3-methyl-2-butenyl)coumarin (Ex. 29), or 3-cyano-5,7-diethoxycoumarin (Ex. 30).

The results are shown below.

(Ex. 3) 8-Methoxy-3-(1H-tetrazol-5-yl)coumarin

Colorless needles [DMF-H$_2$O (4:1 by volume)]
Melting point: 247° to 249° C. (decomposition)
Analysis for $C_{11}H_8N_4O_3$: Calcd. (%): C 54.10, H 3.30, N 22.94 Found (%): C 53.88, H 3.35, N 22.76.
Infrared absorption spectrum ($\nu_{max}^{KBr}$ cm.$^{-1}$): 3,200 (NH), 1,720 (C=O), 1,625 and 1,610 (C=C)
Mass spectrum (M/e): 244 (M+), 202, 201, 188, 160 and 144

(Ex. 4) 8-Ethoxy-3-(1H-tetrazol-5-yl)coumarin

Colorless flakes [DMF-H$_2$O (5:1 by volume)]
Melting point: 234° to 237° C. (decomposition)
Analysis for $C_{12}H_{10}N_4O_3$: Calcd. (%): C 55.81, H 3.90, N 21.70. Found (%): C 55.73, H 3.94, N 21.59.
Infrared absorption spectrum ($\nu_{max}^{KBr}$ cm.$^{-1}$): 3,150 (NH), 1,710 (C=O), 1,625 and 1,610 (C=C)
Mass spectrum (M/e): 258 (M+), 230, 216, 215, 202 and 174

(Ex. 5) 8-n-Propoxy-3-(1H-tetrazol-5-yl)coumarin

Colorless needles [DMF-H$_2$O (4:1 by volume)]
Melting point: 208° to 209° C. (decomposition
Analysis for $C_{13}H_{12}N_4O_3$: Calcd. (%): C 57.35, H 4.44, N 20.58. Found (%): C 57.17, H 4.47, N 20.31.
Infrared absorption spectrum ($\nu_{max}^{KBr}$ cm.$^{-1}$): 3,175 (NH), 1,725 (C=O), 1,625, 1,610 and 1,585 (C=C)
Mass spectrum (M/e): 272 (M+), 230, 188, 187, 174 and 146

(Ex. 6) 8-Isopropoxy-3-(1H-tetrazol-5-yl)coumarin

Colorless needles [DMF-H$_2$O (4:1 by volume)]
Melting point: 200° C.:(decomposition)
Analysis for $C_{13}H_{12}N_4O_3$: Calcd. (%): C 57.35, H 4.44, N 20.58. Found (%); C 57.03, H 4.61, N 20.29.
Infrared absorption spectrum ($\nu_{max}^{KBr}$ cm.$^{-1}$): 3,150 (NH), 1,700 (C=O), 1,615, 1,600 and 1,575 (C=C)
Mass spectrum (M/e): 272 (M+), 257, 230, 202, 188, 187, 174, 146 and 128

(Ex. 7) 7-n-Propoxy-3-(1H-tetrazol-5-yl)coumarin

Colorless needles [DMF-H$_2$O (5:1 by volume)]
Melting point: 237° to 238° C. (decomposition)
Analysis for $C_{13}H_{12}N_4O_3$: Calcd. (%): C 57.35, H 4.44, N 20.58. Found (%): C 57.26, H 4.49, N 20.36.
Infrared absorption spectrum ($\nu_{max}^{KBr}$ cm.$^{-1}$): 3,200 (NH), 1,700 (C=O), 1,620, 1,595 and 1,570 (C=C)
Mass spectrum (M/e): 272 (M+), 230, 216, 202, 188, 174 and 146

(Ex. 8) 8-n-Butoxy-3-(1H-tetrazol-5-yl)coumarin

Colorless needles [DMF-H$_2$O (5:1 by volume)]
Melting point: 198° to 199° C. (decomposition)
Analysis for $C_{14}H_{14}N_4O_3$: Calcd. (%): C 58.73, H 4.93, N 19.57. Found (%); C 58.54, H 495, N 19.35.
Infrared absorption spectrum ($\nu_{max}^{KBr}$ cm.$^{-1}$): 3,200 (NH), 1,725 (C=O), 1,625, 1,605 and 1,580 (C=C)
Mass spectrum (M/e): 286 (M+), 272, 230, 203, 202, 188, 187, 174, 146 and 128

(Ex. 9) 8-Isopentyloxy-3-(1H-tetrazol-5-yl)coumarin

Colorless needles [DMF-H$_2$O (5:1 by volume)]
Melting point: 203° to 204° C. (decomposition)
Analysis for $C_{15}H_{16}N_4O_3$: Calcd. (%): C 59.99, H 5,37, N 18.66. Found (%): C 59.73, H 5.39, N 18.45.
Infrared absorption spectrum ($\nu_{max}^{KBr}$ cm.$^{-1}$): 3,200 (NH), 1,725 (C=O), 1,625, 1,600 and 1,580 (C=C)
Mass spectrum (M/e): 300 (M+), 285, 284, 257, 231, 230 203, 187 and 146

(Ex. 10) 8-n-Hexyloxy-3-(1H-tetrazol-5-yl)coumarin

Colorless needles [DMF-H$_2$O (5:1 by volume)]
Melting point: 191° C. (decomposition)
Analysis for $C_{16}H_{18}N_4O_3$: Calcd. (%): C 61.13, H 5.77, N 17.83. Found (%): C 60.96, H 5.80, N 17.61.
Infrared absorption spectrum ($\nu_{max}^{KBr}$ cm.$^{-1}$): 3,150 (NH), 1,725 (C=O), 1,625, 1,605 and 1,580 (C=C)
Mass spectrum (M/e): 314 (M+), 231, 230, 203, 187, 174 and 146

(Ex. 11) 8-n-Heptyloxy-3-(1H-tetrazol-5-yl)coumarin

Colorless needles (ethyl acetate)
Melting point: 165° C. (decomposition)
Analysis for $C_{17}H_{20}N_4O_3$: Calcd. (%): C 62.18, H 6.14, N 17.06. Found (%): C 62.07, H 6.23, N 17.00.
Infrared absorption spectrum ($\nu_{max}^{KBr}$ cm.$^{-1}$): 3,200 (NH), 1,725 (C=O), 1,625, 1,610 and 1,580 (C=C)
Mass spectrum (M/e): 328 (M+), 286, 230, 146 and 118

(Ex. 12) 8-n-Nonyloxy-3-(1H-tetrazol-5-yl)coumarin

Colorless needles (ethyl acetate)
Melting point: 179° C. (decomposition)
Analysis for $C_{19}H_{24}N_4O_3$: Calcd. (%): C 64.02, H 6.79 N 15.72. Found (%): C 63.87, H 6.88, N 15.63.
Infrared absorption specturum ($\nu_{max}^{KBr}$ cm.$^{-1}$): 3,180 (NH), 1,730 (C=O), 1,625, 1,605 and 1,580 (C=C)
Mass spectrum (M/e): 356 (M+), 314, 230, 146 and 118

(Ex. 13) 8-n-Dodecyloxy-3-(1H-tetrazol-5-yl)coumarin

Colorless needles (ethyl acetate/benzene=1:1 by volume)
Melting point: 180° to 181° C. (decomposition)
Analysis for $C_{22}H_{30}N_4O_3$: Calcd. (%): C 66.31, H 7.59, N 14.06. Found (%): C 66.18, H 7.64, N 13.97.
Infrared absorption specturum ($\nu_{max}^{KBr}$ cm.$^{-1}$): 3,160 (NH), 1,725 (C=O), 1,625, 1,610 and 1,580 (C=C)
Mass spectrum (M/e): 398 (M+), 356, 230 and 146

(Ex. 14) 8-n-Pentadecyloxy-3-(1H-tetrazol-5-yl)coumarin

Colorless needles (ethyl acetate/benzene=1/1 by volume)
Melting point: 169° C. (decomposition)

Analysis for $C_{25}H_{36}N_4O_3$: Calcd. (%): C 68.15, H 8.24, N 12.72. Found (%): C 68.02, H 8.31, N 12.63.

Infrared absorption spectrum ($\nu_{max}^{KBr}$ cm.$^{-1}$): 3,180 (NH), 1,730 (C=O), 1,625, 1,610 and 1,580 (C=C)

Mass spectrum (M/e): 440 (M+), 398, 230, 188, 187 and 146.

(Ex. 15)
8-n-Octadecyloxy-3-(1H-tetrazol-5-yl)coumarin

Colorless needles (ethyl acetate/benzene=1/1 by volume)

Melting point: 166° C. (decomposition)

Analysis for $C_{28}H_{42}N_4O_3$: Calcd. (%): C 69.67, H 8.77, N 11.61. Found (%): C 69.49, H 8.86, N 11.57.

Infrared absorption specturum ($\nu_{max}^{KBr}$ cm.$^{-1}$): 3,200 (NH), 1,725 (C=O), 1,630, 1,610 and 1,580 (C=C)

Mass spectrum (M/e): 482 (M+), 440, 230 and 146

(Ex. 16) 8-Allyloxy-3-(1H-tetrazol-5-yl)coumarin

Colorless needles [DMF-H₂O (5:1 by volume)]
Melting point: 200° C. (decomposition)
Analysis for $C_{13}H_{10}N_4O_3$: Calcd. (%): C 57.77, H 3.73, N 20.73. Found (%): C 57.45, H 3.81, N 20.40.

Infrared absorption spectrum ($\nu_{max}^{KBr}$ cm.$^{-1}$): 3,225 (NH), 1,710 (C=O), 1,625, 1,610 and 1,580 (C=C)

Mass spectrum (M/e): 270 (M+), 227 and 187

(Ex. 17) 8-Geranyloxy-3-(1H-tetrazol-5-yl)coumarin

Light yellow needles (ethyl acetate)
Melting point: 159° C. (decomposition)
Analysis for $C_{20}H_{22}N_4O_3$: Calcd. (%): C 65.55, H 6.05, N 15.29. Found (%): C 65.42, H 6.17, N 15.08.

Infrared absorption specturum ($\nu_{max}^{KBr}$ cm.$^{-1}$): 3,180 (NH), 1,725 (C=O), 1,625, 1,610 and 1,580 (C=C)

Mass spectrum (M/e): 366 (M+), 230, 146 and 118

(Ex. 18) 8-Farnesyloxy-3-(1H-tetrazol-5-yl)coumarin

Light yellow needles (benzene)
Melting point: 132° C. (decomposition)
Analysis for $C_{25}H_{30}N_4O_3$: Calcd. (%): C 69.10, H 6.96, N 12.90. Found (%): C 68.96, H 7.04, N 12.77.

Infrared absorption spectrum ($\nu_{max}^{KBr}$ cm.$^{-1}$): 3,200 (NH), 1,730 (C=O), 1,625, 1,610 and 1,580 (C=C)

Mass spectrum (M/e): 434 (M+), 230 and 146

(Ex. 19) 8-Hydroxy-3-(1H-tetrazol-5-yl)coumarin

Colorless needles [DMF-H₂O (4:1 by volume)]
Melting point: 295° to 296° C. (decomposition)
Analysis for $C_{10}H_6N_4O_3$: Calcd. (%): C 52.18, H 2.63, N 24.34. Found (%): C 52.06, H 2.75, N 24.07.

Infrared absorption spectrum ($\nu_{max}^{KBr}$ cm.$^{-1}$): 3,450 (OH), 3,150 (NH), 1,705 (C=O) and 1,620 (C=C)

Mass spectrum (M/e): 230 M+), 188, 187, 174 and 146

(Ex. 20)
8-Ethoxy-6-methyl-3-(1H-tetrazol-5-yl)coumarin

Light yellow needles [DMF-H₂O (5:1 by volume)]
Melting point: 253° C. (decomposition)
Analysis for $C_{13}H_{12}N_4O_3$: Calcd. (%): C 57.35, H 4.44, N 20.58. Found (%): C 57.18, N 4.46, N 20.43.

Infrared absorption spectrum ($\nu_{max}^{KBr}$ cm.$^{-1}$): 3,200 (NH), 1,720 (C=O), 1,645, 1,625 and 1,585 (C=C)

Mass spectrum (M/e): 272 (M+), 244, 230, 229, 202, 201, 188, 160 and 144

(Ex. 21)
6-Methyl-8-n-propoxy-3-(1H-tetrazol-5-yl)coumarin

Light yellow needles [DMF-H₂O (5:1 by volume)]
Melting point: 229° C. (decomposition)
Analysis for $C_{14}H_{14}N_4O_3$: Calcd. (%): C 58.73, H 4.93, N 19.57. Found (%): C 58.58, H 4.98, N 19.34.

Infrared absorption spectrum ($\nu_{max}^{KBr}$ cm.$^{-1}$): 3,250 (NH), 1,720, 1,710 (C=O), 1,630 and 1,590 (C=C)

Mass spectrum (M/e): 286 (M+), 244, 202, 201, 188, 160 and 132

(Ex. 22)
8-Isopropoxy-6-methyl-3-(1H-tetrazol-5-yl)coumarin

Light yellow needles [DMF-H₂O (5:1 by volume)]
Melting point: 208° C. (decomposition)
Analysis for $C_{14}H_{14}N_4O_3$: Calcd. (%): C 58.73, H 4.93, N 19.57. Found (%): C 58.65, H 4.96, N 19.45.

Infrared absorption spectrum ($\nu_{max}^{KBr}$ cm.$^{-1}$): 3,200 (NH), 1,705 (C=O), 1,620, 1,600 and 1,585 (C=C)

Mass spectrum (M/e): 286 (M+), 244, 202, 201, 188, 160 and 132

(Ex. 23)
6-Ethyl-7-methoxy-3-(1H-tetrazol-5-yl)coumarin

Light yellow needles [DMF-H₂O (5:1 by volume)]
Melting point: 241° C. (decomposition)
Analysis for $C_{13}H_{12}N_4O_3$: Calcd. (%): C 57.35, H 4.44, N 20.58. Found (%): C 57.22, H 4.58, N 20.31.

Infrared absorption spectrum ($\nu_{max}^{KBr}$ cm.$^{-1}$): 3,350 (NH), 1,705 (C=O), 1,610 and 1,570 (C=C)

Mass spectrum (M/e): 272 (M+), 229, 216, 188 and 173

(Ex. 24)
7-Methoxy-8-methyl-3-(1H-tetrazol-5-yl)coumarin

Colorless needles [DMF-H₂O (5:1 by volume)]
Melting point: 282° to 283° C. (decomposition)
Analysis for $C_{12}H_{10}N_4O_3$: Calcd. (%): C 55.81, H 3.90, N 21.70. Found (%): C 55.65, H 3.98, N 21.43.

Infrared absorption spectrum ($\nu_{max}^{KBr}$ cm.$^{-1}$): 3,150 (NH), 1,695 (C=O), 1,600 and 1,575 (C=C)

Mass spectrum (M/e): 258 (M+), 216, 215, 202, 187, 174 and 144

(Ex. 25)
6-Methoxy-7-methyl-3-(1H-tetrazol-5-yl)coumarin

Colorless needles [DMF-H₂O (5:1 by volume)]
Melting point: 298° C.
Analysis for $C_{12}H_{10}N_4O_3$: Calcd. (%): C 55.81, H 3.90, N 21.70. Found (%): C 55.69, H 3.94, N 21.50.

Infrared absorption spectrum ($\nu_{max}^{KBr}$ cm.$^{-1}$): 3,275 (NH), 1,740, 1,710 (C=O), 1,615 and 1,570 (C=C)

Mass spectrum (M/e): 258 (M+), 216, 215, 202, 187 and 174

(Ex. 26)
8-Allyloxy-6-methyl-3-(1H-tetrazol-5-yl)coumarin

Light yellow needles [DMF-H₂O (5:1 by volume)]
Melting point: 211° to 212° C. (decomposition)
Analysis for $C_{14}H_{12}N_4O_3$: Calcd. (%): C 59.15, H 4.26, N 19.71. Found (%): C 59.06, H 4.31, N 19.54.

Infrared absorption spectrum ($\nu_{max}^{KBr}$ cm.$^{-1}$): 3,250 (NH), 1,700 (C=O), 1,650, 1,620 and 1,580 (C=C)

Mass spectrum (M/e): 284 (M+), 241, 201, 200, 199 and 159

(Ex. 27)
8-Hydroxy-6-methyl-3-(1H-tetrazol-5-yl)coumarin

Yellow needles [DMF-H$_2$O (5:1 by volume)]
Melting point: 258° to 259° C. (decomposition)
Analysis for C$_{11}$H$_8$N$_4$O$_3$: Calcd. (%): C 54.11, H 3.30, N 22.94. Found (%): C 53.93, H 3.35, N 22.83.
Infrared absorption spectrum ($\nu_{max}^{KBr}$ cm.$^{-1}$): 3,450 (OH), 3,200 (NH), 1,680 (C=O), 1,610 and 1,590 (C=C)
Mass spectrum (M/e): 244 (M+), 202, 201, 188, 187, 160 and 132

(Ex. 28)
7-Methoxy-6-(3-methyl-2-butenyl)-3-(1H-tetrazol-5-yl)coumarin

Light yellow needles [DMF-H$_2$O (4:1 by volume)]
Melting point: 213° C. (decomposition)
Analysis for C$_{16}$H$_{16}$N$_4$O$_3$: Calcd. (%): C 61.53, H 5.16, N 17.94. Found (%): C 61.27; H 5.28, N 17.71.
Infrared absorption spectrum ($\nu_{max}^{KBr}$ cm.$^{-1}$): 3,225 (NH), 1,705 (C=O), 1,605 and 1,575 (C=C)
Mass spectrum (M/e): 312 (M+), 197, 181, 170, 169 and 153

(Ex. 29)
7-Ethoxy-6-(3-methyl-2-butenyl)-3-(1H-tetrazol-5-yl)coumarin

Light yellow needles [DMF-H$_2$O (4:1 by volume)]
Melting point: 219° C. (decomposition)
Analysis for C$_{17}$H$_{18}$N$_4$O$_3$: Calcd. (%): C 62.56, H 5.56, N 17.17. Found (%): C 62.53, H 5.60, N 17.08.
Infrared absorption spectrum ($\nu_{max}^{KBr}$ cm.$^{-1}$): 3,225 (NH), 1,700 (C=O), 1,610 and 1,570 (C=C)
Mass spectrum (M/e): 326 (M+), 311, 297, 284, 283, 242, 227 and 215

(Ex. 30) 5,7-Diethoxy-3-(1H-tetrazol-5-yl)coumarin

Yellow needles [DMF-H$_2$O (5:1 by volume)]
Melting point: 280° C. (decomposition)
Analysis for C$_{14}$H$_{14}$N$_4$O$_4$: Calcd. (%): C 55.62, H 4.67, N 18.54. Found (%): C 55.47, H 4.72, N 18.36.
Infrared absorption spectrum ($\nu_{max}^{KBr}$ cm.$^{-1}$): 3,250 (NH), 1,690 (C=O), 1,620, 1,600 and 1,575 (C=C)
Mass spectrum (M/e): 302 (M+), 274, 260, 259, 246, 218, 190 and 162

EXAMPLE 31

[Sodium salt of 8-n-butoxy-3-(1H-tetrazol-5-yl)coumarin]

In 5 ml. of a saturated aqueous solution of sodium hydrogencarbonate was dissolved 0.5 g. of 8-n-butoxy-3-(1H-tetrazol-5-yl)coumarin obtained in Example 8 with heating. The solution was allowed to stand at room temperature, and the resulting precipitate was filtered and dried to give 0.4 g. of sodium salt of 8-n-butoxy-3-(1H-tetrazol-5-yl)coumarin in the form of colorless powder. The melting point was not less than 300° C.

EXAMPLE 32

[Diisopropylamine salt of 8-n-butoxy-3-(1H-tetrazol-5-yl)coumarin]

In 20 ml. of ethanol was dissolved 0.5 g. of 8-n-butoxy-3-(1H-tetrazol-5-yl)coumarin obtained in Example 8 with heating. After adding 2 ml. of diisopropylamine to the solution, it was agitated at 40° C. for 5 minutes. Ethanol and excess diisopropylamine were then evaporated under reduced pressure. The residue was washed by adding dried ether thereto, filtered and dried to give 0.55 g. of colorless powder of diisopropylamine salt of 8-n-butoxy-3-(1H-tetrazol-5-yl)coumarin. The melting point was 187° to 190° C. (decomposition).

EXAMPLE 33

[Sodium salt of 8-isopropoxy-6-methyl-3-(1H-tetrazol-5-yl)coumarin]

In 5 ml. of a saturated aqueous solution of sodium hydrogencarbonate was heat-dissolved 0.5 g. of 8-isopropoxy-6-methyl-3-(1H-tetrazol-5-yl)coumarin obtained in Example 22, and the solution was allowed to stand at room temperature. The resulting precipitate was then filtered and dried to give 0.35 g. of colorless powder of sodium salt of 8-isopropoxy-6-methyl-3-(1H-tetrazol-5-yl)coumarin. The melting point was not less than 300° C.

EXAMPLE 34

[Diisopropylamine salt of 8-isopropoxy-6-methyl-3-(1H-tetrazol-5-yl)coumarin]

In 15 ml. of ethanol was heat-dissolved 0.5 g. of 8-isopropoxy-6-methyl-3-(1H-tetrazol-5-yl)coumarin obtained in Example 22. After adding 2 ml. of diisopropylamine to the solution, it was agitated at 40° C. for 5 minutes. Ethanol and excess diisopropylamine were then evaporated under reduced pressure. The residue was washed by adding dried ether thereto, filtered and dried to give 0.55 g. of colorless powder of diisopropylamine salt of 8-isopropoxy-6-methyl-3-(1H-tetrazol-5-yl)coumarin. The melting point was 193° to 196° C. (decomposition).

EXAMPLE 35

A mixture of 5 parts of 8-n-butoxy-3-(1H-tetrazol-5-yl)coumarin, 30 parts of lactose, 45 parts of corn starch, 15 parts of a microcrystalline cellulose (commercially available under the registered trade mark "Avicel" made by Asahi Chemical Industry Co., Ltd.), 3 parts of methyl cellulose and 2 parts of magnesium stearate was thoroughly blended and then screened through a 50 mesh screen. The resulting powder was tabletted by an automatic tabletting machine to give tablets containing 5 mg. of the essential active ingredient per one tablet.

EXAMPLE 36

The procedures of Example 35 were repeated to give 29 kinds of tablets containing 5 mg. of the essential active ingredient per one tablet except that there were employed instead of 8-n-butoxy-3-(1H-tetrazol-5-yl)coumarin respectively, 8-n-pentyloxy-3-(1H-tetrazol-5-yl)coumarin, 8-n-butoxy-6-methyl-3-(1H-tetrazol-5-yl)coumarin, 8-methoxy-3-(1H-tetrazol-5-yl)coumarin, 8-ethoxy-3-(1H-tetrazol-5-yl)coumarin, 8-n-propoxy-3-(1H-tetrazol-5-yl)coumarin, 8-isopropoxy-3-(1H-tetrazol-5-yl)coumarin, 7-n-propoxy-3-(1H-tetrazol-5-yl)coumarin, 8-isopentyloxy-3-(1H-tetrazol-5-yl)coumarin, 8-n-pentyloxy-3-(1H-tetrazol-5-yl)coumarin, 8-n-heptyloxy-3-(1H-tetrazol-5-yl)coumarin, 8-n-nonyloxy-3-(1H-tetrazol-5-yl)coumarin, 8-n-dodecyloxy-3-(1H-tetrazol-5-yl)coumarin, 8-n-pentadecyloxy-3-(1H-tetrazol-5-yl)coumarin, 8-n-octadecyloxy-3-(1H-tetrazol-5-yl)coumarin, 8-allyloxy-3-(1H-tetrazol-5-yl)coumarin, 8-geranyloxy-3-(1H-tetrazol-5-yl)coumarin, 8-farnesyloxy-3-(1H-tetrazol-5- yl)coumarin, 8-hydroxy-3-(1H-tetrazol-5-yl)coumarin, 8-ethoxy-6-methyl-3-(1H-tetrazol-5-yl)coumarin, 6-methyl-8-n-propoxy-3-(1H-tetrazol-5-yl)coumarin, 8-isopropoxy-6-methyl-3-(1H-tetrazol-5-yl)coumarin, 6-ethyl-7-methoxy-3-(1H-tetrazol-5-yl)coumarin, 7-methoxy-8-methyl-3-(1H-tetrazol-5-yl)coumarin, 6-methoxy-7-methyl-3-(1H-tetrazol-5-yl)coumarin, 8-allyloxy-6-methyl-3-(1H-tetrazol-5-yl)coumarin, 8-hydroxy-6-methyl-3-(1H-tetrazol-5-yl)coumarin, 7-methoxy-6-(3-methyl-2-butenyl)-3-(1H-tetrazol-5-yl)coumarin, 7-ethoxy-6-(3-methyl-2-butenyl)-3-(1H-tetrazol-5-yl)coumarin and 5,7-diethoxy-3-(1H-tetrazol-5-yl)coumarin.

EXAMPLE 37

A mixture of 5 parts of 8-n-hexyloxy-3-(1H-tetrazol-5-yl)coumarin, 55 parts of lactose, 30 parts of corn starch, 8 parts of Avicel and 2 parts of magnesium stearate was thoroughly blended. The mixture was then filled in capsules made of gelatin to give capsules containing 5 mg. of the essential active ingredient per one capsule.

EXAMPLE 38

The procedures of Example 37 were repeated except that 8-n-heptyloxy-3-(1H-tetrazol-5-yl)coumarin, 8-n-nonyloxy-3-(1H-tetrazol-5-yl)coumarin, 8-n-dodecyloxy-3-(1H-tetrazol-5-yl)coumarin, 8-n-pentadecyloxy-3-(1H-tetrazol-5-yl)coumarin, 8-n-octadecyloxy-3-(1H-tetrazol-5-yl)coumarin, 8-geranyloxy-3-(1H-tetrazol-5-yl)coumarin and 8-farnesyloxy-3-(1H-tetrazol-5-yl)coumarin were employed respectively instead of 8-n-hexyloxy-3-(1H-tetrazol-5-yl)coumarin to give 7 kinds of capsules containing 5 mg. of the essential active ingredient per one capsule.

EXAMPLE 39

The tablets obtained in Example 35 were crushed and then screened through a 50 mesh screen and a 100 mesh screen to give granules having a particle size of 50 to 100 meshes which contained 50 mg. of the essential active ingredient per 1 g. of granules.

EXAMPLE 40

The same mixture as in Example 37 was prepared and finely pulverized. The obtained powder was then screened through a 100 mesh screen to give powders having an average particle size of 120 meshes which contained 50 mg. of the essentiall active ingredient per 1 g. of powders.

EXAMPLE 41

In 1,000 ml. of a physiological salt solution was dissolved 2 g. of 8-isopropoxy-6-methyl-3-(1H-tetrazol-5-yl)coumarin sodium salt. The solution was adjusted to pH 7.4 to give an injection.

EXAMPLE 42

A nasal drops was prepared by dissolving in 1,000 ml. of distilled water 2 g. of 8-n-butoxy-3-(1H-tetrazol-5-yl)coumarin sodium salt, 0.1 g. of methyl p-hydroxybenzoate, 0.1 g. of butyl p-hydroxybenzoate and 7.5 g. of sodium chloride.

EXAMPLE 43

According to the following formulation, an aerosol was prepared as follows:

| | |
|---|---|
| 8-n-Hexyloxy-3-(1H-tetrazol-5-yl)coumarin | 0.5% |
| Ethanol | 29.5% |
| Dichlorodifluoromethane (propellant) | 42.0% |
| 1,2-Dichlorotetrafluoroethane (propellant) | 28.0% |

8-n-Hexyloxy-3-(1H-tetrazol-5-yl)coumarin was dissolved in ethanol, and the solution was placed in a container for aerosol. The propellant was then supplied to the container through a valve nozzle under pressure until the pressure became 2.5 to 3.5 kg./cm.$^2$G at 20° C.

EXAMPLE 44

With respect to the present 3-(1H-tetrazol-5-yl)coumarin derivatives, there was tested antiallergic activity concerning passive cutaneous anaphylaxis (PCA) mediated by homocytotropic antibodies (HTA) in rats.

(1) Methods (i) Preparation of antisera 2,4-Dinitrophenyl-coupled ascaris extract (DNP-As) used as antigen, was prepared according to the methods of Strejan et al [cf. J. Immunol., Vol. 98, 893(1967)] and Eisen [cf. J. Amer. Chem. Soc., Vol. 75. 4593(1953)]. Antisera containing HTA were prepared in rats according to the method of Tada and Okumura [cf. J. Immunol., Vol. 106, 1002(1971)] as follows:

Female wister rats weighing 180 to 200 g. were splenectomized and several days later immunized by injecting into all four footpads a total of 1 mg. of DNP-As mixed with $10^{10}$ Bordetella pertussis. After 5 days, 0.5 mg. of DNP-As alone was injected subcutaneously into the back of rats. Eight days after the first immunization, blood was collected by aortic puncture under ether anaesthesea and antisera obtained by these procedures were pooled and stored at −80° C.

The titer of the pooled autiserum was determined in rats by the 72 hr. PCA which method was described in the following item (ii), i.e. the highest dilution of antiserum producing a diameter of approximately 5 mm. was usually 1:500.

(ii) Assessment of PCA in rats

Normal wister rats weighing 140 to 160 g. were sensitized passively by injection intradermal on the shaved back skin 0.05 ml. of the diluted antisera (1:30). After 72 hours, the animals were injected intravenously 1 ml. of physiological salt solution containing 2 mg. DNP-As and 2.5 mg. Evans' blue.

The present compounds to be tested were given orally 30 minutes before antigen challenge. The animals were exsanguinated 30 minutes after challenge with the antigens and the skins were exfoliated. The intensities of PCA were evaluated by measuring the amount of leaked dye. The amount of dye leaked as a result of PCA was extracted according to the method of Harada et al [cf. Jpn. J. Allergol., Vol. 15, 1(1966)] and measured photometrically. The lowest doses of the present compounds to be tested which decreased statistically significantly the amount of leaked dye comparing with control, were expressed as the minimum effect dose (MED).

(2) Results

The results obtained on the PCA are shown in Table 3.

TABLE 3

| Compound | MED (mg./kg.) |
| --- | --- |
| Ex. 1 | 1.56 |
| 2 | 0.39 |
| 3 | 6.25 |
| 4 | 6.25 |
| 5 | 6.25 |
| 6 | 1.56 |
| 7 | 6.25 |
| 8 | 1.56 |
| 31 (Na salt of Ex. 8) | 1.56 |
| 9 | 0.39 |
| 10 | 1.56 |
| 11 | 1.56 |
| 12 | 6.25 |
| 13 | 6.25 |
| 14 | 6.25 |
| 15 | 6.25 |
| 16 | 1.56 |
| 17 | 6.25 |
| 18 | 6.25 |
| 19 | 25.00 |
| 20 | 1.56 |
| 21 | 1.56 |
| 22 | 1.56 |
| 23 | 1.56 |
| 24 | 6.25 |
| 25 | 12.50 |
| 26 | 1.56 |
| 27 | 12.50 |
| 28 | 1.56 |
| 29 | 12.50 |
| 30 | 12.50 |

EXAMPLE 45

With respect to the present 3-(1H-tetrazol-5-yl)coumarin derivatives, there was tested acute toxicity in mice.

After normal female Slc: ddy mice 4 weeks old were purchased and fed preliminarily in this lavoratory for a week, these mice weighing 25–27 g. were used in the test. The present compounds to be tested, were suspended in a 10% gum arabic solution and administered orally 0.1 ml./kg. body weight to mice. Each dose level was given to a group of ten animals and the survivors were kept under observation for 6 days. The numbers of dead animals were counted and the $LD_{50}$ values in mg./kg. body weight were calculated by the method of Litchfield-Wilcoxon.

The results are shown in Table 4.

TABLE 4

| Compound | $LD_{50}$ (mg./kg.) |
| --- | --- |
| Ex. 1 | 1330 |
| 2 | 1870 |
| 3 | 2000–3000 |
| 4 | 2500 |
| 5 | 2000–3000 |
| 6 | 2250 |
| 7 | 2000–3000 |
| 8 | 2380 |
| 31 (Na salt of Ex. 8) | 2470 |
| 9 | 1000–2000 |
| 10 | 2650 |
| 11 | 2000–3000 |
| 12 | 2000–3000 |
| 13 | 2000–3000 |
| 14 | 2000–3000 |
| 15 | 2000–3000 |
| 16 | 2000–3000 |
| 17 | 500–1000 |
| 18 | 1000–2000 |
| 19 | 2000–3000 |
| 20 | 2360 |
| 21 | 1000–2000 |
| 22 | 2200 |
| 23 | 500–1000 |
| 24 | 300–1000 |
| 25 | 500–1000 |
| 26 | 2000–3000 |
| 27 | 2000–3000 |
| 28 | 500–1000 |
| 29 | 500–1000 |
| 30 | 2000–3000 |

What we claim is:

1. A coumarin derivative of the formula:

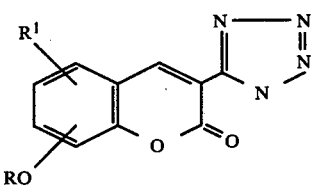

wherein R is a normal pentyl group, a normal hexyl group, and a normal heptyl group, the OR group being positioned on the 8 position of the coumarin ring, and wherein $R^1$ is hydrogen or methyl, said $R^1$ being positioned on the 6 position of the coumarin ring.

2. 8-n-hexyloxy-3-(1H-tetrazol-5-yl)coumarin.
3. 8-n-hexyloxy-3-(1H-tetrazol-5-yl)coumarin.
4. 8-n-heptyloxy-3-(1H-tetrazol-5-yl)coumarin.
5. A pharmaceutical composition having an anti-allergic activity which comprises, as the essential active ingredient, an effective amount of a coumarin derivative of the following general formula:

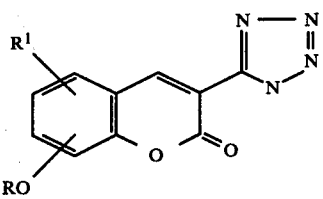

wherein R is a normal pentyl group, a normal hexyl group, and a normal heptyl group, the OR group being positioned on the 8 position of the coumarin ring, and wherein $R^1$ is hydrogen or methyl, said $R^1$ being positioned on the 6 position of the coumarin ring, or a pharmaceutically acceptable salt of said coumarin derivative and a pharmaceutically acceptable carrier.

6. A pharmaceutical composition having an anti-allergic activity which comprises, as the essential active ingredient, an effective amount of a coumarin derivative selected from the group consisting of 8-n-pentyloxy-3-(1H-tetrazol-5-yl)-coumarin, 8-n-hexyloxy-3-(1H-tetrazol-5-yl)-coumarin, and 8-n-heptyloxy-3-(1H-tetrazol-5-yl)-coumarin or a pharmaceutically acceptable salt of said coumarin derivative and a pharmaceutically acceptable carrier.

* * * * *

UNITED STATES PATENT AND TRADEMARK OFFICE
CERTIFICATE OF CORRECTION

PATENT NO. : 4,363,812

DATED : December 14, 1982

INVENTOR(S) : KURIYAMA ET AL

It is certified that error appears in the above-identified patent and that said Letters Patent are hereby corrected as shown below:

Column 2, line 32, "tert-phenyl" should read --tert-pentyl-- and Column 24, line 34, "8-n-hexyloxy-3-(1H-tetrazol-5-yl)coumarin" should read -- 8-n-pentyloxy-3-(1H-tetrazol-5-yl)coumarin --.

Signed and Sealed this

Thirty-first Day of May 1983

[SEAL]

Attest:

DONALD J. QUIGG

Attesting Officer

Acting Commissioner of Patents and Trademarks